United States Patent [19]

Miller et al.

[11] 4,378,357

[45] Mar. 29, 1983

[54] NOVEL HETEROCYCLIC COMPOUNDS

[75] Inventors: George A. Miller, Maple Glen; Lendon N. Pridgen, Lansdale, both of Pa.

[73] Assignee: Rohm and Haas Company, Philadelphia, Pa.

[21] Appl. No.: 861,468

[22] Filed: Dec. 16, 1977

Related U.S. Application Data

[63] Continuation-in-part of Ser. No. 765,146, Feb. 3, 1977.

[51] Int. Cl.$^3$ ............... C07D 263/08; C07D 265/06; C07D 265/08; A01N 43/72; A01N 43/78; A01N 43/86; C07D 263/04

[52] U.S. Cl. .................................... 424/244; 546/278; 546/280; 548/262; 548/136; 548/143; 548/336; 548/144; 548/182; 548/348; 548/183; 548/187; 548/225; 548/215; 548/238; 548/226; 548/228; 260/330.6; 424/248.4; 424/248.52; 424/248.53; 424/248.54; 424/246; 424/263; 424/269; 424/272; 544/88; 544/96; 544/97; 544/333; 544/360; 544/369; 544/371; 544/405; 544/58.5; 544/58.6; 544/58.7; 544/122; 544/123; 544/133; 544/134; 544/137; 546/275

[58] Field of Search ................ 260/307 F, 330.6, 333; 424/272, 248.4, 248.52-248.54, 244; 544/53, 54, 88, 112, 88, 97; 71/88, 90, 92; 548/238, 215, 226, 225, 266, 268

[56] References Cited

U.S. PATENT DOCUMENTS 3,682,948  8/1972  Tomilia et al. .................... 544/88
3,879,524  4/1975  Wehmeister .................. 260/307 F
4,124,591 11/1978  Eicken et al. ....................... 71/88

FOREIGN PATENT DOCUMENTS 2205514  5/1974  France .
527558  10/1972  Switzerland ..................... 424/272

Primary Examiner—Mary C. Lee
Assistant Examiner—D. B. Springer
Attorney, Agent, or Firm—Polly E. Ramstad; Alex R. Sluzas

[57] ABSTRACT

This invention relates to novel heterocyclic fungicides which are effective in controlling a broad spectrum of phytopathogenic fungi found in the four main classes of fungi namely Phycomycetes, Ascomycetes, Fungi Imperfecti, and Basidiomycetes. Certain of these compounds are especially effective in controlling sclerotial forming fungi such as *Whetzelinia sclerotiorum* = (*Sclerotinia sclerotiorium*) and *Botrytis cinerea*.

44 Claims, No Drawings

NOVEL HETEROCYCLIC COMPOUNDS

SUMMARY OF THE INVENTION

This application is a continuation-in-part of U.S. patent application Ser. No. 765,146 filed Feb. 3, 1977.

This invention relates to novel heterocyclic fungicides useful in controlling a number of agriculturally important plant diseases caused by phytopathogenic fungi. Certain of these compounds are particularly useful in controlling sclerotial forming fungi such as *Whetzelinia sclerotiorium* (*Sclerotinia sclerotiorium*) and *Botrytis cinerea*.

In particular, this invention relates to heterocyclic compounds of the formula

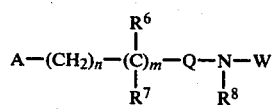

(I)

wherein
A is a group of the formula

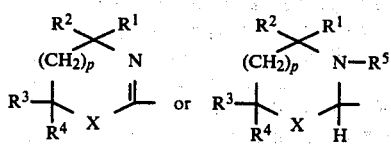

wherein $R^1$, $R^2$, $R^3$ and $R^4$ are independently
(1) hydrogen;
(2) ($C_1$–$C_8$) alkyl optionally substituted with up to three halogens or ($C_1$–$C_4$) alkoxy;
(3) phenyl optionally substituted with up to two substituents independently selected from the group consisting of halogen, nitro, trihalomethyl, ($C_1$–$C_4$) alkoxy and ($C_1$–$C_4$) alkyl;
(4) ($C_2$–$C_8$) alkenyl, preferably ($C_2$–$C_4$) alkenyl, more preferably allyl;
(5) ($C_2$–$C_8$) alkynyl, preferably ($C_2$–$C_4$) alkynyl, more preferably propargyl;
(6) ($C_1$–$C_8$) alkoxy, preferably ($C_1$–$C_2$) alkoxy, more preferably methoxy;
(7) ($C_1$–$C_8$) alkylthio, preferably ($C_1$–$C_2$) alkylthio, more preferably methylthio;
(8) ($C_1$–$C_8$) alkylsulfinyl, preferably ($C_1$–$C_2$) alkylsulfinyl, more preferably methylsulfinyl;
(9) ($C_1$–$C_8$) alkylsulfonyl, preferably ($C_1$–$C_2$) alkylsulfonyl, more preferably methylsulfonyl;
(10) ($C_1$–$C_4$) dialkylamino, preferably di($C_1$–$C_2$) alkylamino, more preferably dimethylamino;
(11) ($C_1$–$C_8$) alkylcarbonyl, preferably ($C_1$–$C_4$) alkylcarbonyl, more preferably acetyl;
(12) phenylcarbonyl optionally substituted with up to two substituents independently selected from the group consisting of halogen, nitro, trihalomethyl, ($C_1$–$C_4$) alkoxy and ($C_1$–$C_4$) alkyl; or
(13) when taken together with the carbon atoms to which they are attached form a benzene ring; and X is O, S or $NR^a$ wherein $R^a$ is hydrogen, ($C_1$–$C_8$)alkyl, phenyl, benzyl, p-toluenesulfonyl or methylsulfonyl;
p is 0, 1, 2 or 3; and
$R^5$ is ($C_1$–$C_3$) alkyl; or A is a group of the formula

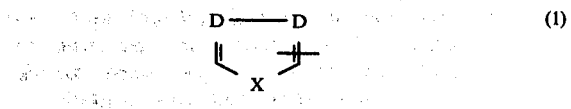

wherein X is O, S or $NR^a$ and D is N or CH;

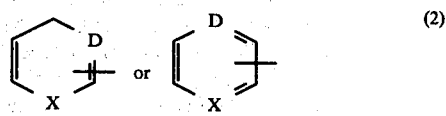

wherein X is O, S or $NR^a$ and D is N or CH;

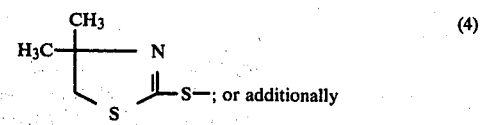

when n and m are zero then A is

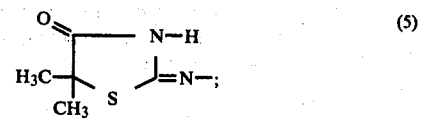

$R^6$ and $R^7$ are independently
(1) hydrogen;
(2) ($C_1$–$C_8$) alkyl, preferably ($C_1$–$C_4$) alkyl more preferably methyl;
(3) ($C_3$–$C_8$) cycloalkyl, preferably ($C_5$–$C_7$) cycloalkyl, more preferably cyclohexyl;
(4) ($C_2$–$C_8$) alkenyl, preferably ($C_2$–$C_4$) alkenyl, more preferably allyl;
(5) ($C_5$–$C_8$) cycloalkenyl, preferably ($C_5$–$C_7$) cycloalkenyl, more preferably cyclohexenyl;
(6) ($C_2$–$C_8$) alkynyl, preferably ($C_2$–$C_4$) alkynyl, more preferably propargyl;
(7) phenyl optionally substituted with up to two substituents selected from the group consisting of halogen, nitro, trihalomethyl, ($C_1$–$C_4$) alkoxy, and ($C_1$–$C_4$) alkyl;
(8) pyridyl;
(9) naphthyl; or
$R^6$ and $R^7$ can be taken together to form a ($C_5$–$C_8$) cycloalkyl group;
$R^8$ is hydrogen or ($C_1$–$C_3$) alkyl;
Q is the group

wherein Y and Z are independently O, S or NH; or
Q is the group

wherein T is O, S or NH; and $R^9$ is
(1) hydrogen;

(2) ($C_1$-$C_8$) alkyl, preferably ($C_1$-$C_4$) alkyl, more preferably methyl; or
(3) phenyl optionally substituted with up to two substituents independently selected from the group consisting of halogen, nitro, trihalomethyl, ($C_1$-$C_4$) alkoxy and ($C_1$-$C_4$) alkyl;

W is selected from the group consisting of
(a) phenyl optionally substituted with up to four substituents, preferably with up to two substituents, independently selected from the group consisting of halogen, nitro, trihalomethyl, ($C_1$-$C_4$) alkyl, ($C_1$-$C_4$) alkoxy, ($C_1$-$C_4$) alkylthio, ($C_1$-$C_4$) alkylsulfinyl, ($C_1$-$C_4$) alkylsulfonyl, di($C_1$-$C_2$) alkylamino, ($C_1$-$C_4$) alkylcarbonyl and phenyl carbonyl;
(b) pyridyl;
(c) pyrimidyl;
(d) diphenylether;
(e) naphthyl; and
(f) furyl;
n is zero to five;
m is zero or one; and
the stabile agronomically acceptable acid addition salts, alkyl halide salts, alkali metal and alkaline earth salts metal salt complexes, enantiomorphs and racemic mixtures thereof.

A preferred embodiment of this invention is the compounds according to Formula (I) wherein
A is a group of the formula

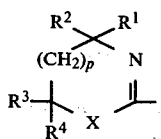

wherein $R^1$, $R^2$, $R^3$ and $R^4$ are independently
(1) hydrogen;
(2) ($C_1$-$C_8$) unsubstituted alkyl;
(3) unsubstituted phenyl;
(4) ($C_2$-$C_4$) alkenyl;
(5) ($C_2$-$C_4$) alkynyl;
(6) ($C_1$-$C_2$) alkoxy;
(7) ($C_1$-$C_2$) alkylthio;
(8) ($C_1$-$C_2$) alkylsulfinyl;
(9) ($C_1$-$C_2$) alkylsulfonyl;
(10) di($C_1$-$C_2$) alkylamino;
(11) ($C_1$-$C_4$) alkylcarbonyl; or
(12) unsubstituted phenylcarbonyl;
X is O, S or $NR^a$ wherein $R^a$ is hydrogen or ($C_1$-$C_8$) alkyl;
p is zero or the integer one or two;
$R^6$ and $R^7$ are independently
(1) hydrogen;
(2) ($C_1$-$C_4$) alkyl;
(3) ($C_5$-$C_7$) cycloalkyl
(4) ($C_2$-$C_4$) alkenyl;
(5) ($C_5$-$C_7$) cycloalkenyl;
(6) ($C_2$-$C_4$) alkynyl; or
(7) unsubstituted phenyl;
$R^8$ is hydrogen or ($C_1$-$C_3$) alkyl;
Q is the group

wherein Y and Z are independently O, S or NH;
W is phenyl optionally substituted with up to two substituents independently selected from the group consisting of halogen, nitro, trihalomethyl, ($C_1$-$C_4$)alkyl, ($C_1$-$C_4$) alkoxy, ($C_1$-$C_4$) alkylthio, ($C_1$-$C_4$) alkylsulfinyl, ($C_1$-$C_4$) alkylsulfonyl, di($C_1$-$C_4$) alkylamino, ($C_1$-$C_4$) alkylcarbonyl and phenyl carbonyl;
n is zero or an integer from one to three; and
m is zero or the integer one.

A more preferred embodiment of this invention is the compounds according to Formula (I) wherein
A is a group of the formula

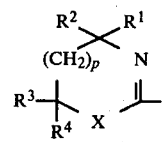

wherein $R^1$, $R^2$, $R^3$ and $R^4$ are independently hydrogen, ($C_1$-$C_8$) unsubstituted alkyl, unsubstituted phenyl, allyl, propargyl, methoxy, methylthio, methylsulfinyl, methylsulfonyl, dimethylamino, acetyl or unsubstituted phenylcarbonyl; X is O, S or $NR^a$ wherein $R^a$ is hydrogen or methyl; p is zero or the interger one; $R^6$ and $R^7$ are independently hydrogen, ($C_1$-$C_4$) alkyl, cyclohexyl, vinyl or allyl, cyclohexenyl, propargyl, or unsubstituted phenyl; $R^8$ is hydrogen or methyl; Q is the group

wherein Y and Z are independently O, S or NH; W is phenyl substituted with up to two substituents selected from the group consisting of halogen, nitro, trifluoromethyl, methyl, methoxy, methylthio, methylsulfinyl, methylsulfonyl, dimethylamino, acetyl and benzoyl; n is zero or the integer one; and m is the integer one.

A most preferred embodiment of this invention is the compounds of the formula

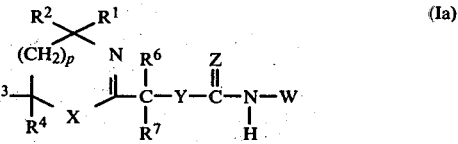

(Ia)

wherein $R^1$, $R^2$, $R^3$ and $R^4$ are independently hydrogen, methyl or ethyl, more preferably $R^1$ and $R^2$ are methyl and $R^3$ and $R^4$ are hydrogen; X is O, S, NH or $NCH_3$, more preferably O; p is zero or the integer one, more preferably zero; $R^6$ and $R^7$ are independently hydrogen, ($C_1$-$C_4$) alkyl, allyl, propargyl, or unsubstituted phenyl, more preferably hydrogen or methyl; Y is O, S or NH; Z is O; W is phenyl substituted with up to two substituents selected from the group consisting of halogen, methyl, methoxy and trifluoromethyl, more preferably substituted with up to two halogen atoms.

In the definition of $R^1$, $R^2$, $R^3$, $R^4$, $R^5$, $R^6$, $R^7$, $R^8$ and $R^9$ as used in the present specification and claims the terms "alkyl", "alkenyl", and "alkynyl" are meant to include both branched and straight chained groups.

Compounds of the present invention can be prepared by general synthetic routes. Certain of the heterocyclic alcohols utilized as starting materials in this invention are commercially available or are known in the art. Methods for the preparation of some of these alcohols are disclosed in South African Pat. No. 727,999 granted Nov. 13, 1973; U.S. Pat. No. 3,542,699 granted Nov. 24, 1970; *Journal of Organic Chemistry*, 41, (9), 1642-4 (1976); *Chemical Reviews*, 71, 483-505, (1971); *Liebig's Annals de Chemie*, 183-202 (1976); and *Journal of the American Chemical Society*, 80,2214 (1958) and these methods are incorporated herein by reference. The alcohol, mercaptan and amine starting materials wherein $R^1$, $R^2$, $R^3$, $R^4$, $R^5$, $R^6$, x, y, p and n are as defined in Formula I can be prepared by the following general route.

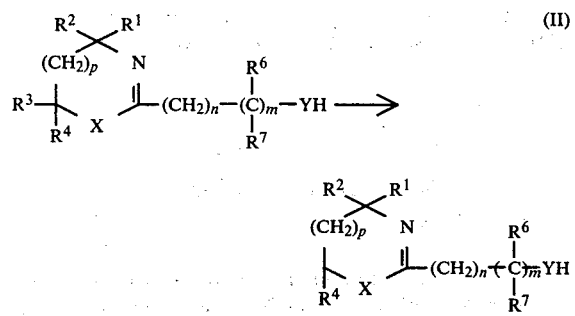

This thermal condensation of the amine and the acid can be performed either in an inert solvent such as mesitylene, xylene, toluene benzene, dimethylsulfoxide, dimethylformamide and the like, or it can be performed in a neat solution at temperatures from about 20° to 200° C., preferably from about 80° to 160° C.

These same alcohols, mercaptans and amines can also be prepared by the following general route.

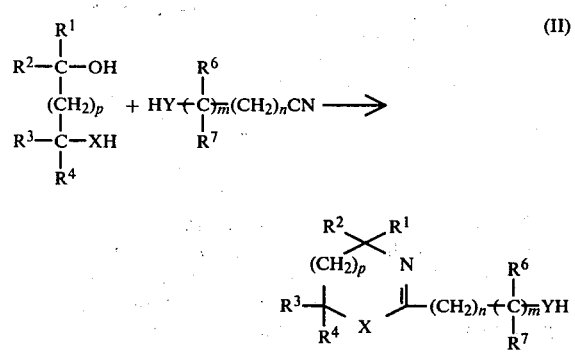

This reaction is preferably performed by adding the appropriate alcohols, preferably wherein $R^4$ is a hydrogen atom, to the appropriate nitrile in concentrated sulfuric acid at or below 10° C.

The starting materials of this invention wherein X is 0 or S can also be prepared by first taking an appropriate substituted alkene and converting it to a halohydrin via reaction with halogens in the presence of water. Alternatively, an appropriately substituted epoxide can also be converted to a halohydrin via treatment with halogen acid. The halohydrin can be converted to the halomercaptan via treatment with phosphorous pentasulfide. The halohydrin or halomercaptan is then reacted with an appropriate cyanohydrin in the presence of a suitable acid scavenger such as sodium or potassium carbonate, or a tertiary amine to form the appropriate heterocyclic alcohol or mercaptan. The solvents which can be utilized in the above sequence of reactions include any inert solvent such as xylene, benzene, toluene, dimethylformamide and the like. The temperatures under which these reactions can be run are from about 0° C. to about 150° C. preferably from about 50° C. to about 110° C.

The alcohol starting materials of this invention wherein X is 0, S or $NR^a$, $R^a$ being other than hydrogen and $R^1$, $R^2$, $R^3$, $R^4$, $R^6$ and $R^7$ are as defined in Formula I are depicted by the following general synthetic route:

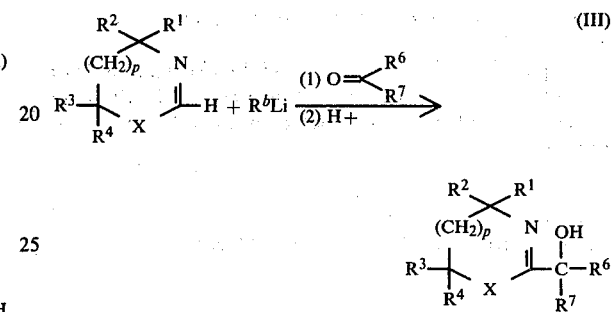

wherein $R^b$ is ($C_1$-$C_8$) alkyl, phenyl, benzyl and the like.

The labile hydrogen in the 2 position of the heterocyclic ring is first metalated in an anhydrous solvent such as diethyl ether, tetrahydrofuran, diglyme and the like and is then reacted with an appropriate ketone or aldehyde followed by treatment with a mineral acid to yield the appropriate alcohol starting material. This reaction can also be used to metalate the aromatic heterocyclic rings encompassed by this invention. The alcohol can then be halogenated with a halogenating agent such as thionyl chloride, N-bromo- or chlorosuccinimide, phosphorous pentachloride or bromide and the like in an inert anhydrous solvent such as benzene, toluene, xylene and the like at temperatures from about 0° to 110° C. The resultant halide can then be converted to an amine via reaction with ammonia or an amine either neat or in an inert solvent such as diethyl ether, tetrahydrofuran and the like at temperatures from about 0° to about 110° C. The alcohol starting material can be converted to the mercaptan by reaction with phosphorous pentasulfide at temperatures from about 80° to about 200° C., preferably from about 100° to 150° C. either neat or in an inert solvent such as benzene, toluene, xylene and the like. This sequence of reactions to convert the alcohol to the mercaptan and the amine can also be utilized on the Formula II and III alcohols as well as the Formula IV alcohol given below.

The alcohol starting materials of the present invention wherein X is 0, S or NH and $R^6$ and $R^7$ are as defined under Formula II can be prepared by the following synthetic route.

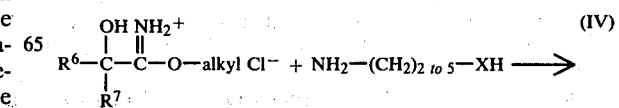

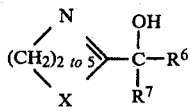

The α-hydroxy imidate ester is prepared by bubbling anhydrous hydrogen chloride into a solution of the appropriate α-hydroxynitrile and an equivalent amount of an alkyl alcohol in an anhydrous solvent such as diethyl ether, tetrahydrofuran and the like at temperatures at or below 20° C., preferably below 5° C. This α-hydroxyimidate is then reacted with the appropriate amine to give the desired heterocyclic alcohol starting material. These alcohols can then be converted to the amine or mercaptan as discussed above under Formula III.

Preparation of the 2-imino-azolidin-4-one alcohols of the present invention wherein X is O, S or NR$^a$, R$^a$ being other than hydrogen, is depicted by the following general synthetic route

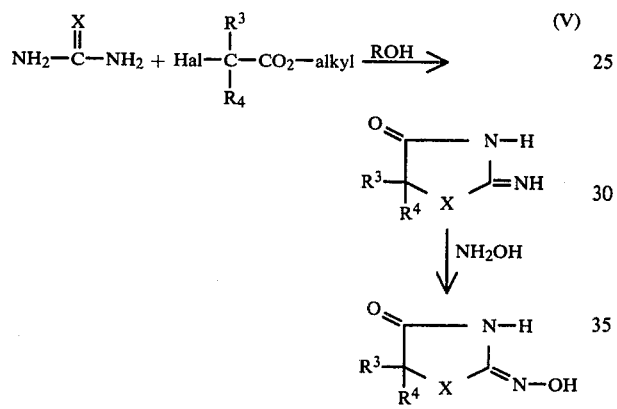

This reaction is performed in alcoholic solvents such as methanol, propanol and the like at temperatures from about 50° C. to about 100° C., preferably at about 80° C. The diazolinone alcohols can be prepared by reacting an appropriately substituted α-hydroxy carboxylic acid ester wherein X is O or S with hydrazine followed by reaction with phosgene or thiophosgene to form the desired product of Formula VI.

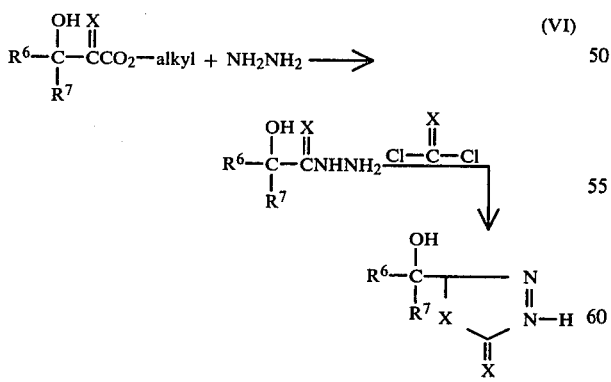

This reaction can be carried out in solvents such as acetonitrile, benzene, xylene and the like at temperatures from about 20° C. to about 110° C.

The starting materials of Formula II, III and IV can be reacted with (C$_1$–C$_3$) alkyl iodide in an appropriate anhydrous solvent such as diethyl ether, tetrahydrofuran and the like to give the alkyl iodide salt of the formula

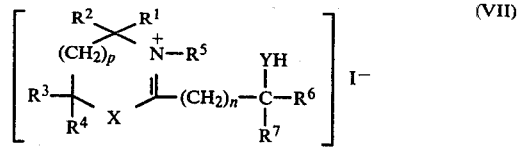

This iodide salt can be reduced to the saturated heterocyclic compounds of Formula VIII by reduction with a metal hydride such as sodium hydride, lithium aluminum hydride, sodium borohydride and the like in an anhydrous solvent such as diethyl ether, tetrahydrofuran and the like at temperatures from about 0° to about 100° C. preferably at about room temperature.

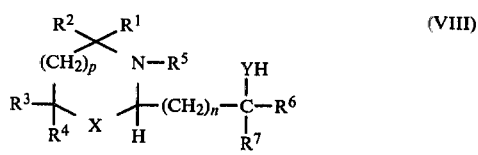

The carbamate compounds of the present invention wherein A, n, R$^6$, R$^7$, R$^8$, m, Y, Z and W are as defined in Formula I can be prepared by the following general synthetic route.

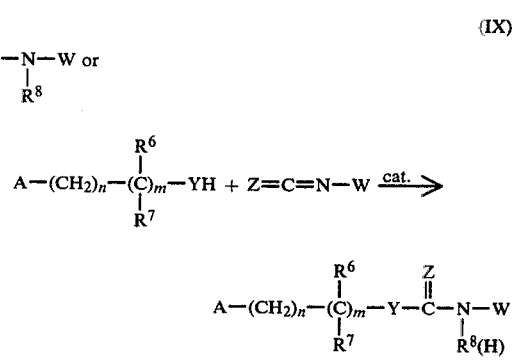

The heterocyclic alcohol, mercaptan or amine is reacted in an anhydrous solvent such as benzene, toluene or xylene with an arylisocyanate, isothiocyanate N-substituted carbamoyl or thiocarbamoyl chloride at temperatures from about 20° C. to 120° C. with or without an appropriate catayst such as triethylamine or 2-ethyl stannous hexanoate to give the appropriate heterocyclic compound of Formula I.

The arylisocyanate, isothiocyanate, N-substituted carbamoyl or thiocarbamoyl chloride are prepared by reacting an appropriately substituted aniline or N-substituted aniline with phosgene or thiophosgene in an anhydrous solvent such as benzene, toluene, xylene and the like at temperatures from about room temperature to about 120° C.

The heterocyclic amine can be reacted with an appropriately substituted aryl pseudothiourea, either neat or in a solvent such as tetrahydrofuran, dioxane, dimethylformamide and the like, at temperatures from about 80° to about 150° C. to form the product according to Formula IX wherein Y and Z ar both NH.

When the heterocyclic compound of Formula IX wherein Z is O or S is reacted with phosphorous pentahalide in an anhydrous solvent such as benzene, toluene, xylene and the like at temperatures from about 20° to about 150° C., preferably from about 60° to about 120° C., the halo imidate is formed which upon reaction with an appropriate R⁹TH group at temperatures from about 20° to about 100° C. in a solvent such as chloroform, acetonitrile, dimethylformamide and the like gives a product of Formula X.

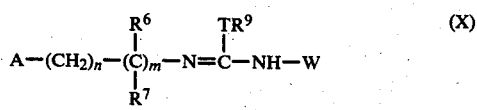

When the heterocyclic compound of Formula IX wherein Y and Z are O or S and R⁸ is hydrogen is metalated in an inert solvent such as diethyl ether, tetrahydrofuran, glyme, dioxane and the like with a base such as sodium hydride, potassium tertiary butoxide, alkyl, phenyl or benzyllithium and the like at temperatures from about −60° to about 100° C., preferably from about 0° to about 50° C., and then reacted with a R⁹ halide the following product of Formula XI is formed.

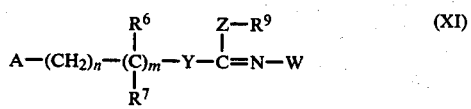

The acid addition salts of the heterocyclic compounds of Formula IX, X and XI can be formed by methods well known in the art. For example, the heterocyclic compound can be dissolved in an appropriate solvent such as methanol, ethanol, propanol and the like and subsequently treated with an equimolar or excess amount of a mineral or organic acid, either neat or dissolved in an appropriate solvent such as methanol, ethanol, propanol and the like, at temperatures from about 0° to about 100° C. followed by evaporation of the solvent and isolation of the salt by standard procedures such as recyrstallization, extraction and the like. Typical acids that can be utiilized in this procedure include hydrochloric, nitric, sulfuric, perchloric, phosphoric, acetic, oxalic, malic, citric, tartaric, p-toluenesulfonic, methylsulfonic and the like.

Certain of the heterocyclic compounds of this invention possess asymmetric carbon atoms. The d and l pairs can be separated via standard techniques such as fractional crystallization with d-tartaric acid, l-tartaric acid, l-quinic acid and the like followed by basification and extraction of the active heterocyclic d or l free base.

The metal salt complexes of the heterocyclic compounds of Formulas IX, X and XI can be prepared by adding dropwise, with stirring, a stoichiometric amount of a transition metal salt dissolved in an appropriate solvent to the heterocyclic compound dissolved in a similarly appropriate solvent. The reaction mixture is briefly stirred and the solvent is removed under reduced pressure to give the metal salt complex of the respective heterocyclic compound. Identification and purity are determined by elemental analysis.

The metal salt complexes can also be prepared by mixing stoichiometric or excess amounts of the transition metal salt and the heterocyclic compound in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include any polar solvent e.g., water, methanol, ethanol, isopropanol or ethylene glycol and any aprotic dipolar solvent e.g., dimethylsulfoxide, acetonitrile, dimethylformamide, nitromethane or acetone.

The transition metal salt cations utilized in the above procedure are selected from Groups IIA, IVA, VA, IB, IIB, VIB, VIIB, and VIII of the Periodic Table. The more preferred metal cations are those selected from the group consisting of calcium, magnesium, manganese, copper, nickel, zinc, iron, cobalt, tin, cadmium, mercury, chromium, lead and barium.

Any appropriate combination of anions which satisfies the valence of the above cations, e.g., chloride, bromide, iodide, sulfate, bisulfate, phosphate, nitrate, perchlorate, carbonate, bicarbonate, hydrosulfide, hydroxide, acetate, oxalate, malate, maleate, citrate and the like may be utilized as the counterion in the metal salt.

It has also been found that any metal containing fungicides can also act as safening agents when used in place of metal salts. Typical metal containing fungicides that can be utilized in these procedures are:

a. dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb);

b. copper-based fungicides such as: cuprous oxide, copper naphthenate, and Bordeaux mixture; and c. miscellaneous fungicides such as: phenylmercuric acetate n-ethylmercuri-1,2,3,6-tetrahydro-3,6-endomethano-3,4,5,6,7,7-hexachlorophthalimide, phenylmercuri monoethanolammonium lactate, nickel-containing compounds and calcium cyanide.

The procedures outlined above for the preparation of the compounds of the present invention are merely exemplifications of the manner in which these compounds can be synthesized and are not to be considered as the only methods for preparing these compounds. Any of the standard methods of synthesis which are well known to those skilled in the art of synthetic organic chemistry can be utilized in the preparation of the compounds of this invention.

Typical compounds included in the present invention are:

N-Phenyl-1-(1-methylimidazol-2-yl)ethylthiocarbamate
N-3-Pyridyl-8-(furan-2-yl)octyldithiocarbamate
1-(3-Chlorophenyl)-3-(3-thien-2-ylpropyl)thiourea
1-(3-Chlorophenyl)-2-(1-methylpyrrol-2-ylmethyl)isothiourea
1-(3-Chloro-4-methoxyphenyl)-3-(thiazol-2-ylmethyl)quanidine
1-Phenyl-3-[5-(1-methyl-1,3,4-triazol-2-yl)pentyl]urea
N-(3,5-Dichlorophenyl)-5-(pyrimidin-2-yl)pentylcarbamate
N-(4-Trifluoromethylphenyl)-3-(pyrid-2-yl)propylcarbamate
1-Phenyl-3-(5-methoxymethyl-2-oxazolin-2-ylmethyl)thiourea N-Phenyl-[4-(4-chlorophenyl)-2-thiazolin-2-yl]methylmercaptocarbamate
1-Phenyl-2-(1-butyl-2-imidazolin-2-yl)methylisourea
N-(3,5-Dichlorophenyl)-1-(1-methyl-4,4-dimethyloxazolidin-2-yl)ethylcarbamate
1-(3,5-Dichlorophenyl-2-(4-chlorophenyl)-3-(4,4,6-trimethyl-5,6-dihydro-4H-oxazin-2-yl)methylisourea
1-(3-Bromophenyl)-2-octyl-3-(4,4,6-trimethyl-5,6-dihydro-4H-thiazin-2-ylmethyl)isothiourea
1-(3-Trifluoromethylphenyl)-3-methyl-2-(1,4,4,6-tetramethyl-5,6-dihydro-4H-pyrimidin-2-ylmethyl)-quanidine
N-(3,5-Dibromophenyl)-(4-methylthiomethyl-2-oxazolin-2-yl)methylcarbamate
N-(3,5-Dichlorophenyl)-(4-phenylsulfinylmethyl-2-thiazolin-2-yl)methylthiocarbamate
N-(4-Chlorophenyl)-(4-phenylsulfonylmethyl-1-methyl-2-imidazolin-2-yl)methylcarbamate
N-(4-Nitrophenyl)-4-acetonyl-2-oxazolin-2-yl)methylcarbamate
N-(3,5-Dichlorophenyl)-(1-methyl-4-dimethylaminomethyl-2-imidazolin-2-yl)methylcarbamate
N-(2,4,5-Trichlorophenyl)-(4-methoxycarbonyl-2-oxazolin-2-yl)methylcarbamate
cis or trans N-(2,3,4,5-Tetrachlorophenyl-4-methoxymethyl-5-phenyl-2-oxazolin-2-yl)methylcarbamate
N-(3,5-Dichlorophenyl)-[4-(8-methylthiooctyl)-2-oxazolin-2-yl]methylcarbamate
N-Phenyl-[4-(8-phenylsulfinyloctyl-2-oxazolin-2-yl]methylcarbamate
N-Phenyl-[4-(8-phenylsulfonyloctyl)-2-oxazolin-2-yl]methylcarbamate
N-(3-Chlorophenyl)-[4-(7-oxooctyl)-2-oxazolin-2-yl]methylcarbamate
N-(2-Chlorophenyl-[4-(8-dimethylaminooctyl)-1-methyl-2-imidazolin-2-yl]methylcarbamate
N-(2-Chlorophenyl-[4-(8-dimethylaminooctyl)-1-methyl-2-imidazolin-2-yl]methylcarbamate
N-(4-Chlorophenyl)-[4-(8-ethoxycarbonyloctyl)2-oxazolin-2-yl]methylcarbamate
N-Phenyl-(4-acetoxy-2-thiazolin-2-yl)methylcarbamate
N-(4-Chlorophenyl)-(4-octanoyloxy-2-thiazolin-2-yl)methylcarbamate
N-Phenyl-(4-chloromethyl-2-oxazolin-2-yl)methylcarbamate
N-Phenyl-[4-(8-chlorooctyl)-2-oxazolin-2yl]methylcarbamate
N-Phenyl-(4-ethenyl-2-oxazolin-2-yl)methylcarbamate
N-(3,5-Dichlorophenyl)-(4-ethynyl-2-thiazolin-2-yl)methylcarbamate
N-(3,5-Dichlorophenyl)-[4-(8-octynyl)-2-thiazolin-2-yl]methylmercaptocarbamate
N-(3,5-Dichlorophenyl)-[4-(8-octenyl)-2-thiazolin-2-yl]methylmercaptocarbamate
N-(3,5-Dichlorophenyl)-[4-(8-methoxyoctyl)-2-oxazolin-2-yl]methylcarbamate
N-(3,5-Dichlorophenyl)-[4-(4-chlorophenylcarbonyl)-2-oxazolin-2-yl]methylcarbamate
N-(3,5-Dibromophenyl)-4,5,6,7-tetrahydro-1,3-oxazepin-2-yl)methylcarbamate
N-(3,5-Dichlorophenyl)-(4,5,6,7-tetrahydro-1,3-thiazepin-2-ylmethyl)thiocarbamate
N-(4-Chlorophenyl)-(1H-4,5,6,7-tetrahydrodiazepin-2-yl)methylcarbamate
N-(4-Bromophenyl)-(4,5,6,7-tetrahydro-1,3-oxazocin-2-yl)methylcarbamate
N-(4-Chlorophenyl)-(1H-4,5,6,7-tetrahydro-1,3-diazocin-2-yl)methylcarbamate
N-(3,5-Dichlorophenyl)-1-(1-n-butyl-4,4-dimethyloxazolidin-2-yl)ethylcarbamate
N-(3,5-Dichlorophenyl)-2-(4,4-dimethyl)-2-thiazolin-2-yl)thioethylcarbamate
N-(4-Nitrophenyl)-(4,5,6,7-tetrahydro-1,3-thiazocin-2-yl)methylcarbamate
N-(3,5-Dinitrophenyl)-(4,4,6,6-tetramethyl-2-oxazin-2-yl)methylthiocarbamate
N-(2,3-Dichlorophenyl)-(4,4,5,5-tetramethyl-2-oxazolin-2-yl)methylcarbamate
N-(3,5-Dimethoxyphenyl)-(4,5,6,7-tetrahydro-4,4,7,7-tetramethyl-1,3-oxazepin-2-yl)methylthiocarbamate
N-(3,4-Difluorophenyl)-(4,4,5,5-tetraethyl-2-thiazolin-2-yl)methylcarbamate
N-(2,5-Ditrifluoromethylphenyl)-(4,4,6,6-tetraphenyl-2-oxazin-2-yl)ethylthiocarbamate
N-(2,6-Dichloro-4-nitrophenyl))-(4,4,6,6-tetramethoxy-2-thiazolin-2-yl)propylthiocarbamate
N-(3,4-Dimethylphenyl)-(4,5-diallyl-2-oxazolin-2-yl)methylcarbamate
N-(3,5-Ditrifluoromethylphenyl)-(4,4,6,6-tetramethylthiooxazolin-2-yl)methylcarbamate
N-(4-Methylsulfonylphenyl)-(4,5-dimethylsulfonyl-2-thiazolin-2-yl)ethylthiocarbamate
N-(4-methylsulfinylphenyl)-(4,6-dibenzoyl-2-oxazolin-2-yl)methylcarbamate
N-Phenyl-(4,6-dimethylamino-2- thiazolin-2-yl)methylcarbamate
N-Phenyl-(4,4,6,6-tetraceto-2-oxazolin-2-yl)methylcarbamate
N-Phenyl-(4,4,6,6-tetramethylthio-2-oxazolin-2-yl)methylcarbamate
N-Phenyl-4,5,6,7-tetrahydro-(4,4,7,7-tetramethyl-1,3-oxazepin-2-yl)methylcarbamate
and the acid addition salts and metal salt complexes enantiomorphs and racemic mixtures thereof.

The following examples are provided merely to illustrate the methods of preparation of the heterocyclic compounds of this invention. These examples are not to be considered in any way as limitations of the scope of this invention.

EXAMPLE 1

Preparation of N-(3,5-dichlorophenyl)-2-(5,6-dihydro-4,4,6-trimethyl-4H-1,3-oxazin-2-yl)-2-propylcarbamate A. Preparation of 2-(2-hydroxyprop-2-yl)-4,4,6-trimethyl-5,6-dihydro-4H-1,3-oxazine To a 250 ml 3-necked flask with a thermometer, a mechanical stirrer, and a 100 ml addition funnel attached was added 200 ml of concentrated $H_2SO_4$. The acid was cooled to 0°–5° C. with a dry-ice/acetone bath while 51 g (0.6 mole) of the acetone cyanohydrin was added at such a rate so as to maintain the temperature in the −10° to 10° C. range (Note—caution must be exercised in the initial stages of the addition since a vigorous exotherm occurs). After the addition of the nitrile, 59.0 g (0.5 moles) of 2-methyl-2,4-pentanediol was added again at a rate that kept the temperature in the −10° to 10° range (see the previous note). The mixture was stirred for an additional one hour then poured onto crushed ice (∼5° C.). The acidic aqueous solution was then extracted twice with ether and the ether layers discarded. The acidic aqueous layer was then poured into a large beaker which contained ∼400 g of $NaHCO_3$ and ether. The beaker was cooled with an ice-water bath and was not allowed to rise pass 36° (basification with aqueous KOH resulted in more extensive decomposition due to the higher temperature attained). The ether layer was dried over $K_2CO_3$ and concentrated. The residue obtained was distilled at 43° C. (0.5 mm) to yield 24 g (0.13 mole, 26%) of product. The structure of this alcohol was confirmed by I.R. and N.M.R.

B. Preparation of N-(3,5-dichlorophenyl)-2-(5,6-dihydro-4,4,6-trimethyl-4H-1,3-oxazin-2-yl)-2-propylcarbamate To a 250 ml reflux flask containing 100 ml of $CHCl_3$ was added an equal molar amount of 3,5-dichlorophenylisocyanate and 2-[2-hydroxyprop-2-yl]-4,4,6-trimethyl-5,6-dihydro-1,3-oxazine and 3–4 drops of triethylamine. This solution was heated under reflux 6 hours then allowed to cool and stir overnight. The solvent was removed under vacuum and the residue taken up in $CH_2Cl_2$. Any insoluble material was filtered away and hexane added to the filtrate. The solid that crystallized was collected and dried to yield the product; mp 174°–176°. Structure was confirmed by IR, NMR, and elemental analysis.

EXAMPLE 2

Preparation of N-(3,5-dichlorophenyl)-2-(4,4-dimethyl-$\Delta^2$-1,3-oxazolin-2-yl)-2-propylcarbamate A. Preparation of 2-(2-hydroxyprop-2-yl)-4,4-dimethyl-$\Delta^2$-1,3 oxazoline Method A 2-hydroxyisobutyric acid (26.0 g, 0.25 mole) and 2-amino-2-methyl-1-propanol (22.5 g., 0.25 mole) were heated under reflux in a neat solution for one hour at 120° C. (oil bath temperature). The oil bath was then removed and a distilling head was attached to the flask (a 6 cm vigreaux column was initially attached but was removed after the pot temperature lowered). Electric heating tape was wrapped around the neck of the distilling head and azeotropic distillation begun. The oil bath temperature of 200° C. was maintained. The clear oil distillate was taken up in hexane and dried over $MgSO_4$. Concentration of the organic layer and distillation produced the $\alpha$-hydroxyoxazoline, 23.0 g (0.146 mole, 59%); bp 82–85 (~20 mm); Structure was confirmed by IR and NMR.

Method B 2-hydroxyisobutyric acid (26.0 g, 0.25 mole) and 2-amino-2-methyl-1-propanol (22.5 g, 0.25 mole) were heated together in xylene until 10 ml of water had been collected in a Dean-Stark trap (~16 hour). At the end of this time the reaction flask was cooled and the solvent removed under vacuum. The residue obtained was slowly distilled to yield the oxazoline 25.0 g (0.16 mole, 64%); bp 95° C. (~25 mm). Structure was confirmed by IR and NMR.

B. Preparation of N-(3,5-dichlorophenyl)-2-(4,4-dimethyl-$\Delta^2$-1,3-oxazolin-2-yl)-2-propylcarbamate The same procedure as that used in the preparation of Example 1B was used to produce the product in 48% yield; mp 189°–191°. Structure was confirmed by IR, NMR and elemental analysis.

EXAMPLE 3

Preparation of N-(3,5-dimethylphenyl)-2-(5,6-dihydro-4,4,6-trimethyl-4H-1,3-oxazin-2-yl)-2-propylcarbamate Utilizing 3,5-dimethylphenylisocyanate and the procedures in Example 1A and 1B, the desired product was obtained and its structure was confirmed by IR, NMR and elemental analysis.

EXAMPLE 4

Preparation of N-(3,5-dimethoxyphenyl)-2-(5,6-dihydro-4,4,6-trimethyl-4H-1,3-oxazin-2-yl)-2-propylcarbamate Utilizing 3,5-dimethoxyphenylisocyanate and the procedures in Examples 1A and 1B, the desired product was obtained and its structure was confirmed by IR, NMR and elemental analysis.

EXAMPLE 5

Preparation of N-(3,5-dichlorophenyl)-2-(4,4-dimethyl-$\Delta^2$-1,3-oxazolin-2-yl)-2-propylthiocarbamate Utilizing 3,5-dichlorophenylisothiocyanate and the procedures in Example 2A and 2B, the desired product was obtained and its structure was confirmed by IR, NMR and elemental analysis.

EXAMPLE 6

Preparation of N-(3,5-dichlorophenyl)(5,6-dihydro-4,4,6-trimethyl-4H-1,3-oxazin-2-yl)methylcarbamate Utilizing glycolonitrile and the procedure in Example 1A and 1B, the desired product was obtained and its structure was confirmed by IR, NMR and elemental analysis.

EXAMPLE 7

Preparation of N-(3,5-dichlorophenyl)-1-(4,4-dimethyl-$\Delta^2$-1,3-oxazolin-2-yl)-1-ethylcarbamate Utilizing lactic acid and the procedure in Examples 2A and 2B, the desired product was obtained and its structure was confirmed by IR, NMR and elemental analysis.

EXAMPLE 8

Preparation of N-(3,5-dichlorophenyl)(4,4-dimethyl-$\Delta^2$-1,3-oxazolin-B 2-yl)methylcarbamate Utilizing glycolic acid and the procedures in Examples 2A and B, the desired product was obtained and its structure was confirmed by IR, NMR and elemental analysis.

EXAMPLE 9

Preparation of N-(3,5-dichlorophenyl)-2-($\Delta^2$-1,3-thiazolin-2-yl)-2-propylcarbamate A. Preparation of 2-(2-hydroxyprop-2-yl) $\Delta^2$-1,3-thiazoline 2-Aminoethanethiol (7.0 g, 0.09 mole) was dissolved in 50 ml of xylene and 9.45 g (0.09 mole) of $\alpha$-hydroxyisobutyric acid added to the flask. The suspension was heated under reflux until 3 ml of water had evolved. The xylene solution was then distilled to yield 2.0 g (0.0138, 15%) of product: bp 123°–125° C. (20 mm). Structure was confirmed by IR and NMR.

B. Preparation of N-(3,5-dichlorophenyl)-2-($\Delta^2$-1,3-thiazolin-2-yl)-2-propylcarbamate Utilizing the alcohol of Example 9A above and the procedures of Example B 2B, the desired product was obtained in 26% yield; mp 132° C. Structure was confirmed by IR, NMR and elemental analysis.

EXAMPLE 10

Preparation of
N-(3,5-dichlorophenyl)-1-(4,4-dimethyl-$\Delta^2$-1,3-oxazolin-2-yl)-1-nonylcarbamate A. Preparation of 2-(1-hydroxynon-1-yl)-4,4-dimethyl-$\Delta^2$-1,3-oxazoline An equal molar amount of 2-amino-2-methylpropanol and decanoic acid were heated under reflux for 7 hours in xylene. After 1.5 ml of water had azeotroped off, the reaction mixture was distilled to yield 5.3 g (0.022 mole, 67%) of product bp 112°–113° C. (0.2 mm). The structure was confirmed by IR and NMR.

B. Preparation of N-(3,5-dichlorophenyl)-1-(4,4-dimethyl-$\Delta^2$-1,3-oxazolin-2-yl)-1-nonyl carbamate Utilizing the alcohol from Example 10A and the procedures in Example 1B, the desired product was obtained and its structure was confirmed by IR, NMR and elemental analysis.

EXAMPLE 11

Preparation of
N-(3,5-dichlorophenyl)-1-(4,4-dimethyl-$\Delta^2$-1,3-oxazolin-2-yl)-1-cycloheptylcarbamate Utilizing 1-hydroxycycloheptanecarboxylic acid and the procedures in Examples 2A and 2B, the desired product was obtained and its structure was confirmed by IR, NMR and elemental analysis.

EXAMPLE 12

Preparation of
N-(3,5-dichlorophenyl)-$\alpha$-(4,4-dimethyl-$\Delta^2$-1,3-oxazolin-2-yl)-$\alpha$-benzylcarbamate Utilizing ethylmandelate and the procedures in Example 2A and 2B, the desired product was obtained and its structure was confirmed by IR, NMR and elemental analysis.

EXAMPLE 13

Preparation of
N-(3,5-dichlorophenyl)-2-(1,3,4-oxadiazolin-2-(3H)-one-5-yl)-2-propylcarbamate A. Preparation of 2-(2-hydroxyprop-2-yl)-1,3,4-oxadiazolin-2-(3H)-one The 2-hydroxyisobutyric acid hydrazide (prepared from ethyl isobutyrate and hydrazine) was added to 75 ml of acetonitrile and the solution stirred at room temperature. To this solution was added equal molar amount of phosgene in benzene solution. The white solid that separated was filled off and the filtrate concentrated to yield an oil that solidified; mp 78°–81° C. (crude). Structure was confirmed by IR and NMR.

B. Preparation of N-(3,5-dichlorophenyl)-2-(1,3,4-oxadiazolin-2-(3H)-one-5-yl)-2-propylcarbamate The 1,3,4-oxadiazolin-5-one precursor was dissolved in 50 ml of CHCl$_3$ along with three drops of triethylamine and N(3,5-dichlorophenyl)isocyanate in equal molar amounts. The solution was stirred at reflux 18 hour then concentrated to yield a white solid; 0.2 g (23%); mp 96° C. The structure was confirmed by IR, NMR and elemental analysis.

EXAMPLE 14

Preparation of
N-(3,4-dichlorophenyl)-N-(5,5-dimethyl-4-oxo-thiazolidin-2-yl)oximinocarbamate A. Preparation of 5,5-dimethyl-2-imino-1,3-thiazolidin-4-one A suspension of thiourea (19.0 g, 0.25 mole) in 150 ml of ethanol was heated under reflux until all of the thiourea had dissolved. Ethyl 2-bromo-isobutyrate (49.0 g, 0.25 mole) was then added over 10 minutes to the refluxing solution, after which time the solution was heated under reflux for six hours then allowed to stir at ambient temperature 36 hours. The solution was concentrated to dryness and the residue treated with water, then with aqueous NaHCO$_3$ to adjust the pH to 7.0. The precipitated solid was collected by filtration, washed with water and dried to yield 5,5-dimethyl-2-imino-thiazolidin-4-one: mp 252°–254° C.; 15.0 g (0.12 mole, 47%). Structure was confirmed by IR and NMR.

B. Preparation of 2-oximino-5,5-dimethyl-1,3-thiazolidin-4-one 5,5-dimethyl-1,3-thiazolidin-2-imino (8.3 g., 0.065 mole), hydroxylamine HCl (20.0 g, 0.29 mole), pyridine (25.5 g, 0.32 mole) and ethanol (150 mole) were mixed and heated under reflux 2.5 hours and kept at room temperature 16 hours, after which time the volatiles were removed under reduced pressure and the residue treated with water. The precipitate was collected by filtration and recrystallized from ethanol to give the product: 7.0 g (0.048 mole, 74%); mp 198°–200° C. Structure was confirmed by IR and NMR.

C. Preparation of N-(3,5-dichlorophenyl)-N'-(5,5-dimethyl-4-oxo-thiazolidine-2-yl)oximinocarbamate The 2-oximino material (4.0 g, 28 mole) was suspended in CHCl$_3$ along with 3,5-dichlorophenylisocyanate (5.64 g, 30 mml) and 2–3 drops of triethylamine. After standing at ambient temperature four hours, the solvent was removed under reduced pressure and the residual solid recrystallized from benzene/acetone to yield the product; mp 220°–222° C.; 8.5 g (91.4%); Structure was confirmed by IR, NMR and elemental analysis.

EXAMPLE 15

Preparation of
N-(3,5-dichlorophenyl)-2-(1-methylimidazol-2-yl)-2-propylcarbamate A. Preparation of 2-(2-hydroxyprop-2-yl)-1 methylimidazole The 1-methylimidazole was dissolved in dry THF and the solution cooled to 5° C. A 10% excess n-butylithium was added over one hour period with the reaction vessel being maintained at a temperature range of 5°–20° C. under nitrogen. The solution at the end of the addition was homogenous and purplish in color. After stirring two hours at room temperature, the reaction flask was then cooled to ~10° C. and the acetone in dry THF was added slowly with stirring. After the addition the solution was allowed to stir at ambient temperature one hour then poured onto ice-water. The aqueous layer was acidified with dilute HCl and extracted with ether. The aqueous layer was then basified with K$_2$CO$_3$ then extracted with CH$_2$Cl$_2$ several times. The combined and dried CH$_2$Cl$_2$ extracts were concentrated to yield a white solid which was recrystallized from ethyl acetate; mp 128°–129° C. Structure was confirmed by IR and NMR.

B. Preparation of N-(3,5-dichlorophenyl)-2-(1-methylimidazol-2-yl)-2-propylcarbamate Utilizing the alcohol formed in Examples 15A above and the procedures in Example 2B, the desired product was obtained and its structure was confirmed by IR, NMR and elemental analysis.

EXAMPLE 16

Preparation of N-(3,5-dichlorophenyl)-4-phenyl-4-(4,4-dimethyl-$\Delta^2$-1,3-oxazolin-2-yl)-1-buten-4-ylcarbamate A. Preparation of α-hydroxy-α-(4,4-dimethyl-$\Delta^2$-1,3-oxazolin-2-yl)toluene Utilizing ethylmandelate and the procedure of Example 2A the desired product was obtained and its structure was confirmed by IR and NMR.

B. Preparation of 2-benzoyl-4,4-dimethyl-$\Delta^2$-1,3-oxazoline

A solution of the hydroxyoxazoline from Example 16A (10.0 g, 0.05 mole) was dissolved in 500 ml of methylene chloride to which 200 g of activated manganese dioxide was added. After stirring four days at room temperature, the suspension was filtered under vacuum and the solution concentrated to dryness to yield 8.0 g (0.039 mole, 80%) of product. The structure of this product was confirmed by IR and NMR.

C. Preparation of 1-(4,4-dimethyl-$\Delta^2$-1,3-oxazolin-2-yl)-1-phenyl-4-buten-1-ol To an ethereal solution of the oxazoline from Example 16B (1.0 g, 0.005 mole) under nitrogen was added allylmagnesium chloride. The white suspension was allowed to stir overnight without refluxing and was then hydrolyzed with aqueous ammonium chloride. The organic layer was separated and the remaining aqueous solution was extracted with ether several times. After combining and drying the organic layers, the solvent was removed to yield 1.1 g. of product. The product structure was confirmed by IR and NMR.

D. Preparation of N-(3,5-dichlorophenyl)-4-phenyl-4-(4,4-dimethyl-$\Delta^2$-1,3-oxazolin-2-yl)-1-buten-4-ylcarbamate Utilizing the alcohol from Example 16C and the procedures in Example 1B, the desired product was obtained and its structure was confirmed by IR, NMR and elemental analysis.

EXAMPLE 17

Preparation of N-(3,5-dichlorophenyl)-4-phenyl-4-(4,4-dimethyl-$\Delta^2$-1,3-oxazolin-2-yl)-1-butyn-4-ylcarbamate A. Preparation of α-hydroxy-α-(4,4-dimethyl-4,5-dihydro$\Delta^2$-1,3-oxazolin-2-yl)toluene Utilizing ethylmandelate and the procedure of Example 2A the desired product was obtained and its structure was confirmed by IR and NMR.

B. Preparation of 2-benzoyl-4,4-dimethyl-$\Delta^2$-1,3-oxazoline

A solution of the hydroxyoxazoline from Example 16A (10.0 g, 0.05 mole) was dissolved in 500 ml of methylene chloride to which 200 g of activated manganese dioxide was added. After stirring four days at room temperature, the suspension was filtered under vacuum and the solution concentrated to dryness to yield 8.0 g (0.039 mole, 80%) of product. The structure of this product was confirmed by IR and NMR.

C. Preparation of 1-(4,4-dimethyl-$\Delta^2$-1,3-oxozolin-2-yl)-1-phenyl-4-butyn-1-ol Utilizing propargyl magnesium chloride and the procedure in Example 16C the desired product was obtained and its structure was confirmed by IR and NMR.

D. Preparation of N-(3,5-dichlorophenyl)-4-phenyl-4-(4,4-dimethyl-$\Delta^2$-1,3-oxazolin-2-yl) 1-butyn-4-ylcarbamate Utilizing the alcohol from Example 17C and the procedures in Example 1B, the desired product by IR, NMR and elemental analysis.

EXAMPLE 18

Preparation N-(3,5-dichlorophenyl)-α-(4,5,6,7-tetrahydro-1H-1,3-diazepin-2-yl)α-benzylcarbamate hydrochloride A. Preparation of α-(hydroxybenzyl-4,5,6,7-tetrahydro-1H-1,3-diazepine hydrochloride To 200 ml of absolute ethanol was added 1,4-diaminobutane at 0° C. with continuous stirring. To this solution was added an equal molar amount of ethyl mandelimidate hydrochloride. After stirring at 0°–5° C. for two hours, the suspension was heated under reflux 12 hours then cooled and concentrated to remove any traces of NH$_3$. The concentrated solution was acidified by dropwise addition of ethanolic HCl into the suspension which was then concentrated to dryness and the residue recrystallized several times from CH$_3$CN/ether to yield 14.5 g (34%) of product: mp 179°–181° C. Structure was confirmed by IR and NMR.

B. Preparation of N-(3,5-dichlorophenyl)-α-(4,5,6,7-tetrahydro-1H-1,3-diazepin-2-yl)-α-benzylcarbamate hydrochloride The hydrochloride, Example 18A, was dissolved in hot acetonitrile along with three drops of stannous octoate. To this solution was added an equal molar amount of 3,5-dichlorophenyl isocyanate. The solution was heated under reflux six hours then cooled and allowed to stand at room temperature 16 hours. The solid that formed was removed by filtration and dried to yield 1.5 g (56%) of product: mp 185° C. Structure was confirmed by IR, NMR and elemental analysis.

EXAMPLE 19

Preparation of N-(3,5-dichlorophenyl) (4,5-dihydro-1-methylimidazol-2-yl)-1-methylcarbamate Utilizing ethylene diamine and glycolic acid and the procedure in Example 2A followed by the procedure in Example 2B, the desired product was obtained and its structure was confirmed by IR, NMR and elemental analysis.

The following Tables I and II present the structure, melting points and elemental analysis of some of the more important compounds encompassed by the present invention. These tables are presented as examples of some of the compounds which can be prepared by the procedures given in the present specification and are not meant to be limitations on the breadth and scope of this invention.

Table III which is also given below is a list of some of the novel alcohols utilized as intermediates in the preparation of the heterocyclic compounds of the present invention.

TABLE I $$A-(CH_2)_n-(C)_m-Q-N-W$$
with substituents $R^6$, $R^7$ on C and $R^8$ on N

| Example No. | A | n | $R^6$ | $R^7$ | m | Q | $R^8$ | W |
|---|---|---|---|---|---|---|---|---|
| 1 | 4,4,6-trimethyl-5,6-dihydro-1,3-oxazin-2-yl | 0 | $CH_3$ | $CH_3$ | 1 | $-O-C(=O)-$ | H | $3,5Cl-C_6H_3$ |
| 2 | 4,4-dimethyl-4,5-dihydro-1,3-oxazol-2-yl | 0 | $CH_3$ | $CH_3$ | 1 | $-O-C(=O)-$ | H | $3,5Cl-C_6H_3$ |
| 3 | 4,4,6-trimethyl-5,6-dihydro-1,3-oxazin-2-yl | 0 | $CH_3$ | $CH_3$ | 1 | $-O-C(=O)-$ | H | $3,5CH_3-C_6H_3$ |
| 4 | 4,4,6-trimethyl-5,6-dihydro-1,3-oxazin-2-yl | 0 | $CH_3$ | $CH_3$ | 1 | $-O-C(=O)-$ | H | $3,5CH_3O-C_6H_3$ |
| 5 | 4,4-dimethyl-4,5-dihydro-1,3-oxazol-2-yl | 0 | $CH_3$ | $CH_3$ | 1 | $-O-C(=S)-$ | H | $3,5Cl-C_6H_3$ |
| 6 | 4,4,6-trimethyl-5,6-dihydro-1,3-oxazin-2-yl | 0 | H | H | 1 | $-O-C(=O)-$ | H | $3,5Cl-C_6H_3$ |
| 7 | 4,4-dimethyl-4,5-dihydro-1,3-oxazol-2-yl | 0 | $CH_3$ | H | 1 | $-O-C(=O)-$ | H | $3,5Cl-C_6H_3$ |
| 8 | 4,4-dimethyl-4,5-dihydro-1,3-oxazol-2-yl | 0 | H | H | 1 | $-O-C(=O)-$ | H | $3,5Cl-C_6H_3$ |
| 9 | 4,5-dihydro-1,3-thiazol-2-yl | 0 | $CH_3$ | $CH_3$ | 1 | $-O-C(=O)-$ | H | $3,5Cl-C_6H_3$ |
| 10 | 4,4-dimethyl-4,5-dihydro-1,3-oxazol-2-yl | 0 | $C_8H_{17}$ | H | 1 | $-O-C(=O)-$ | H | $3,5Cl-C_6H_3$ |
| 11 | 4,4-dimethyl-4,5-dihydro-1,3-oxazol-2-yl | 0 | $-(CH_2)_6-$ | | 1 | $-O-C(=O)-$ | H | $3,5Cl-C_6H_3$ |

TABLE I-continued

| # | Structure | n | R | R' | m | X | Y | Ar |
|---|---|---|---|---|---|---|---|---|
| 12 | CH3-C(CH3)-N=C-O (oxazoline) | 0 | C6H5 | H | 1 | -O-C(=O)- | H | 3,5Cl—C6H3 |
| 13 | H-N-N=C-O-C(=O) | 0 | CH3 | CH3 | 1 | -O-C(=O)- | H | 3,5Cl—C6H3 |
| 14 | O=C-CH(CH3)(S)-C(CH3)=N-NH (thiazoline) | 0 | — | — | 0 | -O-C(=O)- | H | 3,5Cl—C6H3 |
| 15 | N-methyl imidazole | 0 | CH3 | CH3 | 1 | -O-C(=O)- | H | 3,5Cl—C6H3 |
| 16 | CH3-C(CH3)-N=C-O | 0 | CH2=CH—CH2— | C6H5 | 1 | -O-C(=O)- | H | 3,5Cl—C6H3 |
| 17 | CH3-C(CH3)-N=C-O | 0 | CH3—C≡C— | C6H5 | 1 | -O-C(=O)- | H | 3,5Cl—C6H3 |
| 18 | 7-membered ring with N=C and NH | 0 | C6H5 | H | 1 | -O-C(=O)- | H | 3,5Cl—C6H3 |
| 19 | N-methyl imidazoline | 0 | H | H | 1 | -O-C(=O)- | H | 3,5Cl—C6H3 |
| 20 | CH3-C(CH3)-N=C-O | 0 | CH3 | H | 1 | -O-C(=O)- | H | 3,4 Cl—C6H3 |
| 21 | CH3-C(CH3)-N=C-O | 0 | CH3 | H | 1 | -O-C(=O)- | H | 3Cl—C6H4 |
| 22 | CH3-C(CH3)-N=C-O | 0 | CH3 | H | 1 | -O-C(=O)- | H | 2Cl,5CF3—C6H3 |
| 23 | CH3-C(CH3)-N=C-O | 4 | H | H | 1 | -O-C(=O)- | H | 3,5Cl—C6H3 |

TABLE I-continued

| # | (structure) | n | R | R' | m | (linker) | R'' | Ar |
|---|---|---|---|---|---|---|---|---|
| 24 | H₅C₂−C(=N)−CH(C₆H₅)−O (oxazoline, 2-ethyl-5-phenyl) | 0 | H | H | 1 | −O−C(=O)− | H | 3,5Cl−C₆H₃ |
| 25 | H₃C−C(CH₃)−CH₂−O−C(=N)− | 1 | CH₃ | CH₃ | 1 | −O−C(=O)− | H | 3,5Cl−C₆H₃ |
| 26 | CH₃−C(CH₃)−CH₂−O−C(=N)− | 2 | H | H | 1 | −S−C(=O)− | H | 3,5Cl−C₆H₃ |
| 27 | CH₃−C(CH₃)−CH₂−O−C(=N⁺CH₃) I⁻ | 0 | CH₃ | CH₃ | 1 | −O−C(=O)− | H | 3,5Cl−C₆H₃ |
| 28 | CH₃−C(CH₃)−CH₂−O−C(=N)− | 0 | H | −CH₂CH₃ | 1 | −O−C(=O)− | H | 3,5Cl−C₆H₃ |
| 29 | CH₃−C(CH₃)−CH₂−O−C(=N)− | 0 | CH₃ | −CH₂CH₃ | 1 | −O−C(=O)− | H | 3,5Cl−C₆H₃ |
| 30 | CH₃−C(CH₃)(CH₃)−CH(CH₃)−O−C(=N)− | 0 | H | H | 1 | −NH−C(=O)− | H | 3,5Cl−C₆H₃ |
| 31 | CH₃−C(CH₃)−CH₂−O−C(=N)− | 0 | nC₃H₇ | H | 1 | −OC(=O)− | H | 3,5Cl−C₆H₃ |
| 32 | CH₃−C(CH₃)−CH₂−O−C(=N)− | 0 | nC₄H₉ | H | 1 | −OC(=O)− | H | 3,5Cl−C₆H₃ |
| 33 | CH₃−C(CH₃)−CH₂−O−C(=N)− | 0 | CH₃ | H | 1 | −OC(=O)− | H | 3-CH₃SC₆H₄ |
| 34 | CH₃−C(CH₃)−CH₂−O−C(=N)− | 0 | CH₃ | H | 1 | −OC(=O)− | H | 3,5CF₃C₆H₃ |
| 35 | CH₃−C(CH₃)−CH₂−O−C(=N)− | 0 | CH₃ | H | 1 | −OC(=O)− | H | 3-NO₂C₆H₄ |

TABLE I-continued

| | | | | | | | | |
|---|---|---|---|---|---|---|---|---|
| 36 | CH₃—C(CH₃)(—N=)—O— (oxazoline with CH₃, CH₃) | 0 | $CH_3$ | H | 1 | $-O\overset{O}{\underset{\|}{C}}-$ | H | $3\text{-}CF_3C_6H_4$ |
| 37 | " | 0 | $CH_3$ | H | 1 | $-O\overset{O}{\underset{\|}{C}}-$ | H | $3\text{-}BrC_6H_4$ |
| 38 | " | 0 | $CH_3$ | H | 1 | $-O\overset{O}{\underset{\|}{C}}-$ | H | $3\text{-}FC_6H_4$ |
| 39 | " | 0 | $CH_3$ | H | 1 | $-O\overset{O}{\underset{\|}{C}}-$ | H | $2,6\text{-}Cl-C_6H_3$ |
| 40 | " | 0 | $CH_3$ | H | 1 | $-O\overset{O}{\underset{\|}{C}}-$ | H | $3\text{-}C_6H_5OC_6H_4$ |
| 41 | " | 0 | $CH_3$ | H | 1 | $-O\overset{O}{\underset{\|}{C}}-$ | H | $2,3\text{-}ClC_6H_4$ |
| 42 | " | 0 | $CH_3$ | H | 1 | $-O\overset{O}{\underset{\|}{C}}-$ | H | $C_6H_5$ |
| 43 | " | 0 | $CH_3$ | H | 1 | $-O\overset{O}{\underset{\|}{C}}-$ | H | $C_{10}H_7$ |
| 44 | " | 0 | $CH_3$ | H | 1 | $-O\overset{O}{\underset{\|}{C}}-$ | H | $2CH_3, 3Cl-C_6H_3$ |
| 45 | " | 0 | $CH_3$ | H | 1 | $-O\overset{O}{\underset{\|}{C}}-$ | H | $2,5Cl-C_6H_3$ |
| 46 | " | 0 | $CH_3$ | H | 1 | $-O\overset{O}{\underset{\|}{C}}-$ | H | $2,4,5Cl-C_6H_2$ |

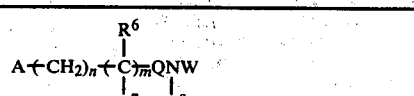

$$A-(CH_2)_n-(\underset{R^7}{\overset{R^6}{\underset{\|}{C}}})_m-QN\underset{R^8}{W}$$

| Example No. | A | n | $R^6$ | $R^7$ | m | Q | $R^8$ | W |
|---|---|---|---|---|---|---|---|---|
| 47 | benzothiazol-2-yl | 0 | $CH_3$ | $CH_3$ | 1 | $-O-\overset{O}{\underset{\|}{C}}-$ | H | $3,5Cl-C_6H_3$ |

TABLE I-continued

| | | | | | | | | | |
|---|---|---|---|---|---|---|---|---|---|
| 48 | $CH_3-\overset{CH_3}{\underset{O}{\overset{|}{C}}}-N\overset{||}{\phantom{i}}$ | 0 | $CH=CH_2$ | $CH_3$ | 1 | $-O-\overset{O}{\overset{||}{C}}-$ | H | $3,5Cl-C_6H_3$ |
| 49 | $CH_3-\overset{CH_3}{\underset{O}{\overset{|}{C}}}-N\overset{||}{\phantom{i}}$ | 1 | $C_{10}H_2$ | H | 1 | $-O-\overset{O}{\overset{||}{C}}-$ | H | $3,5Cl-C_6H_3$ |
| 50 | $CH_3-\overset{CH_3}{\underset{O}{\overset{|}{C}}}-N\overset{||}{\phantom{i}}$ | 1 | $4-CH_3OC_6H_4$ | H | 1 | $-O-\overset{O}{\overset{||}{C}}-$ | H | $3,5Cl-C_6H_3$ |
| 51 | $CH_3-\overset{CH_3}{\underset{O}{\overset{|}{C}}}-N\overset{||}{\phantom{i}}$ | 1 | $C_5H_4N$ | H | 1 | $-O-\overset{O}{\overset{||}{C}}-$ | H | $3,5Cl-C_6H_3$ |
| 52 | $CH_3-\overset{CH_3}{\underset{O}{\overset{|}{C}}}-N\overset{||}{\phantom{i}}$ | 1 | $C_6H_5$ | $C_6H_5$ | 1 | $-O-\overset{O}{\overset{||}{C}}-$ | H | $3,5Cl-C_6H_3$ |
| 53 | $CH_3-\overset{CH_3}{\underset{O}{\overset{|}{C}}}-N\overset{||}{\phantom{i}}$ | 0 | $CH_3$ | H | 1 | $-O-\overset{O}{\overset{||}{C}}-$ | H | $C_4H_3O$ |
| 54 | $CH_3-\overset{CH_3}{\underset{O}{\overset{|}{C}}}-N\overset{||}{\phantom{i}}$ | 0 | $CH_3$ | H | 1 | $-O-\overset{O}{\overset{||}{C}}-$ | H | $3,4,5Cl-C_6H_2$ |

TABLE II

| Example No. | mp °C. | Elemental Analysis Calc'd (Found) | | |
|---|---|---|---|---|
| | | C | H | N |
| 1 | 174–6 | 54.68(54.15) | 5.98(5.61) | 7.53(7.50) |
| 2 | 186–8 | 52.19(52.14) | 5.26(5.36) | 8.11(8.03) |
| 3 | 159–61 | 68.65(68.43) | 8.49(8.79) | 8.43(8.34) |
| 4 | 137–40 | 62.62(63.08) | 7.74(8.05) | 7.69(8.09) |
| 5 | 114–6 | 49.87(49.79) | 5.02(5.17) | 7.75(7.78) |
| 6 | 157–9 | 52.19(52.69) | 5.26(5.28) | 8.11(8.41) |
| 7 | 107–10 | 50.77(50.76) | 4.87(4.87) | 8.46(8.61) |
| 8 | 195 | 49.23(49.00) | 4.45(4.43) | 8.83(8.87) |
| 9 | 148 | 46.86(46.99) | 4.23(4.27) | 8.46(8.57) |
| 10 | 92–4 | 58.74(56.33) | 7.04(6.54) | 6.52(4.82) |
| 11 | 84 | 57.15(56.80) | 6.06(6.20) | 7.02(7.42) |
| 12 | 200 | 58.03(57.79) | 4.61(4.54) | 7.12(6.72) |
| 13 | 96 | 42.25(42.04) | 3.54(3.64) | 12.32(13.24) |
| 14 | 220–2 | 41.37(41.30) | 3.18(3.15) | 12.07(12.06) |
| 15 | 135–6 | 51.21(51.06) | 4.60(4.62) | 12.18(12.97) |
| 16 | 184–6 | 60.98(61.25) | 5.11(5.28) | 6.46(6.81) |
| 17 | 198.99 | 61.26(60.75) | 4.67(4.64) | 6.49(6.75) |
| 18 | 185 | 53.12(53.26) | 4.89(4.89) | 9.78(9.64) |
| 19 | 172–4 | 47.70(47.76) | 4.34(4.35) | 13.91(13.57) |
| 20 | 135–7 | 50.77(51.15) | 4.87(4.97) | 8.46(8.94) |
| 21 | 78–81 | 56.66(57.05) | 5.77(5.85) | 9.94(9.70) |
| 22 | 105–7 | 49.39(49.50) | 4.42(4.50) | 7.68(8.17) |
| 23 | 103—5 | 54.70(54.81) | 59.41(6.05) | 7.50(7.65) |
| 24 | 149–51 | 58.03(57.93) | 4.61(4.76) | 7.12(6.94) |
| 25 | 159–60 | 53.49(53.48) | 5.60(5.67) | 7.80(8.03) |
| 26 | 132–133 | 49.87(49.84) | 5.02(5.06) | 7.75(7.72) |
| 27 | 194–197 | 52.04(51.97) | 6.00(5.20) | 7.92(7.60) |
| 28 | 105–106 | 52.19(52.24) | 5.26(5.41) | 8.10(8.01) |
| 29 | 198–200 | 53.49(53.59) | 5.61(5.72) | 7.80(7.75) |
| 30 | 242–244 | 52.34(52.39) | 5.56(5.79) | 12.21(12.23) |
| 31 | 110° | 53.49(53.59) | 5.60(5.71) | 7.80(7.64) |
| 32 | 110–111 | 54.70(54.81) | 5.94(6.10) | 7.50(7.48) |
| 33 | 107–108 | 58.43(58.42) | 6.54(6.68) | 9.09(9.41) |
| 34 | 138–140 | 48.25(48.05) | 4.08(4.09) | 7.03(6.89) |
| 35 | 124–125 | 54.72(54.50) | 5.58(5.70) | 13.67(13.61) |
| 36 | 105–107 | 54.54(54.58) | 5.19(5.36) | 8.48(8.45) |
| 37 | 107–109 | 49.28(49.14) | 5.02(5.14) | 8.21(8.21) |
| 38 | 93–95 | 59.99(60.34) | 6.11(6.34) | 9.99(9.99) |
| 39 | 112–114 | 50.77(50.57) | 4.87(5.01) | 8.46(8.18) |
| 40 | 99–101 | 67.78(67.90) | 6.26(6.39) | 7.90(7.87) |
| 41 | 88–90 | 50.77(50.77) | 4.87(4.79) | 8.46(8.24) |
| 42 | 81–83 | 64.10(64.20) | 6.92(6.90) | 10.68(10.48) |
| 43 | 110–111 | 69.21(69.32) | 6.45(6.49) | 8.97(8.84) |
| 44 | 94–96 | 57.97(58.14) | 6.16(6.25) | 9.01(9.11) |
| 45 | 101–103 | 50.77(50.66) | 4.87(4.89) | 8.46(8.28) |
| 46 | 120–122 | 45.98(46.02) | 4.37(4.26) | 7.64(7.24) |
| 47 | 125–127 | 53.55(53.88) | 3.70(3.78) | 7.35(7.30) |
| 48 | 168–170 | 53.80(53.99) | 5.08(4.79) | 7.84(8.29) |
| 49 | oil | 63.01(66.04) | 4.85(5.58) | 6.12(6.21) |
| 50 | 159–60 | 57.66(61.83) | 5.07(6.25) | 6.40(7.07) |
| 51 | oil | 55.85(62.38) | 4.69(5.78) | 10.29(11.84) |
| 52 | oil | 62.77(72.09) | 4.86(6.00) | 8.45(5.08) |
| 53 | oil | 57.13 — | 4.59 — | — |
| 54 | 156–8 | 45.98(45.71) | 4.37(4.16) | 7.64(7.62) |

TABLE III

Melting/Boiling Points of Hydroxy 1,3-Heterocycles

| Structure | mp °C | bp °C |
|---|---|---|
| (pyrazole with N-CH₃, N, OH, C(CH₃)₂) | 128–129° | |
| CH₃, CH₃, O, N, OH, C(CH₃)₂ | 51–53° | |
| CH₃, CH₃, CH₃, O, N, OH, C—(CH₃)₂ | | 43°(0.5 mm) |
| CH₃, CH₃, CH₃, O, N, CH₂OH | used crude | |
| CH₃, CH₃, O, N, OH, CH, CH₃ | | 100°(25 mm) |
| CH₃, CH₃, O, N, CH₂OH | | 100–105° (25 mm) |
| S, N, OH, C—(CH₃)₂ | | 123–125° (25 mm) |
| CH₃, CH₃, O, N, OH, C—H, C₈H₁₇ | | 112–138° (0.2 mm) |
| CH₃, CH₃, O, N, OH, C-cyclohexyl | | 93°(0.25 mm) |
| CH₃, CH₃, O, N, OH, C—H, Ph | | 170°(25 mm) |
| CH₃, CH₃, O, N, OH, C—Ph, CH₂—CH=CH₂ | used crude | |

TABLE III-continued

Melting/Boiling Points of Hydroxy 1,3-Heterocycles

| Structure | mp °C | bp °C |
|---|---|---|
| CH₃, CH₃, O, N, OH, C—Ph, C≡C—CH₃ | used crude | |
| N, N, OH H, C, Ph, HCl·H | 179–181° | |
| N, N—CH₃, CH₂OH | | 99–104° (0.4 mm) |
| H—N——N, OH, O, O, C—(CH₃)₂ | 78–81° | |
| CH₃, CH₃, O, N, OH, CH₂—C(CH₃)₂ | used crude | |
| CH₃, CH₃, O, N, OH, C—H, CH₂CH₃ | | 105°(25 mm) |
| CH₃, CH₃, O, N, OH, C—CH₃, CH₂CH₃ | | 120°(25 mm) |
| CH₃, CH₃, O, N, OH, C—H, CH₂CH₂CH₃ | | 150°(20 mm) |
| CH₃, CH₃, CH₃, O, N, CH₂NH₂ | | 58°(0.25 mm) |

Certain of the alcohols, mercaptans and amines of the present invention are novel and useful as starting materials for the preparation of the heterocyclic compounds of the present invention. In particular compounds of the Formula XII and XIII.

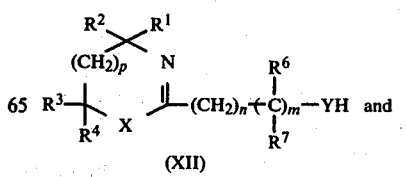

(XII)

-continued

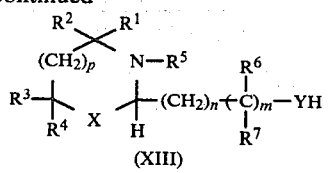

(XIII)

wherein $R^1$ to $R^7$, X, Y, n, m and p are as defined in Formula I with the proviso that in Formula (XII) when Y is oxygen, X is sulfur and when Y is sulfur X is N or S are all novel compounds which are useful as intermediates in the preparation of the fungicidal heterocyclic compounds of the present invention and are thus considered to be a part of the present invention.

The heterocyclic compounds of the present invention possess a high degree of activity against assorted phytophathogenic fungi. Typical fungi which can be controlled by the compounds of this invention include: gray mold (*Botrytis cinerea*) on grape berries (var. Thompson Seedless); broad bean chocolate spot (*Botrytis cinerea*) on broad bean plants; white mold (*Whetzelinia sclerotiorium*) (*Sclerotinia sclerotiroium*) in agar culture; grape downy mildew (*Plasmopora viticola*) on grape plants; bean powdery mildew (*Erysiphe polygoni*) on bean plants, (var. Dwarf Hort); barley net blotch (*Helminthosporium teres*) on barley plants (var. Wong); rice blast (*Piricularia oryzae*) on rice plants, (var. Nova 66); tomato late blight (*Phytophthora infestans*) on tomato plants (var. Rutgers); and wheat stem rust (*Puccinia graminis* f. sp. tritici race 15 B-2) on wheat plants (var. Monon).

In evaluating the compounds of the present invention the fungicidal evaluation is carried out using the compounds at application rates of from about 300 ppm to about 1000 ppm and spraying the plants to run off in a carrier volume of about 150 gallons/acre.

The general procedure is to take potted plants in proper condition of growth for susceptibility to the fungal disease to be evaluated, to spray these under a moving spray boom and allow them to dry. The plants are then inoculated with the appropriate fungal spores and allowed to incubate until the disease has developed and the control is read or estimated. The heterocyclic compounds of the present invention when tested via the above procedure have exhibited complete control of the above phytopathogenic fungi at application rates from about 300 ppm to about 1000 ppm. At application rates as low as 300 ppm certain preferred compounds of this invention were effective in controlling sclerotical forming fungi such as *Botrytis cinerea* and *Whetzelinia sclerotiorium* (*Sclerotinia sclerotiorium*). This activity coupled with the activity against *Plasmopora viticola* makes these compounds particularly useful as fungicides in the wine industry where these fungi are a major problem.

The heterocyclic compounds of the present invention can also be utilized as microbiocides in industrial applications. Typical industrial application in which these compounds can be utilized includes their use as microbiocides in the paint, paper, textile, laundry and cutting oil industries.

The heterocyclic compounds of the present invention can also be utilized as broad spectrum herbicides, particularly as preemergence herbicides on perennial and annual grasses.

Another area of application of the heterocyclic compounds of the present invention are their use as anti-mycotic agents in pharmaceutical and veterinary use. These heterocyclic compounds can be employed as useful anti-mycotic agents in controlling mammalian pathogens. These heterocyclic compounds can also be utilized in controlling gram-negative and gram-positive bacteria.

The heterocyclic compounds of the present invention their acid addition salts and metal salt complexes are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these heterocyclic compounds their acid addition salts or their metal salt complexes can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions extended with water. The concentration of the solution can vary from 1% to 90% with a preferred range being 5 to 50%.

For the preparation of emulsifiable concentrates, the compound can be dissolved in suitable organic solvents, or a mixture of solvents, together with an emulsifying agent which permits dispersion of the fungicides in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of the heterocyclic compound, acid addition salt or metal complex, 45 parts of a synthetic precipitated hydrated silicon dioxide such as that sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate such as that sold under the trademark Zeolex ® 7.

Dusts are prepared by mixing the heterocyclic compound, acid addition salt or metal salt complex with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The heterocyclic compounds, acid addition salt or metal salt complex can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually about 0.1 lb. to 50 lbs. per acre of the active ingredient.

The heterocyclic compounds, acid addition salts or metal salt complexes of this invention can be advantageously employed in various ways. These compounds can be employed in the storage of cereal grain and as fungicides in turf and fruit orchard applications. Other applications of these heterocyclic compounds, acid addition salts and metal salt complexes which suggest themselves to those skilled in the art of agriculture and horticulture are also meant to be encompassed by the spirit and scope of this invention.

We claim:

1. A compound of the formula

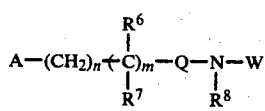

wherein A is a group of the formula

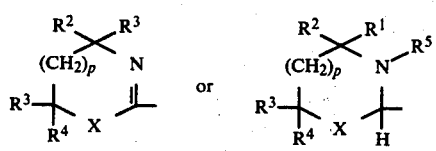

wherein
$R^1$, $R^2$, $R^3$ and $R^4$ are independently hydrogen;
$(C_1-C_3)$ alkyl optionally substituted with up to three halogens or $(C_1-C_3)$ alkoxy;
$(C_2-C_4)$ alkenyl;
$(C_2-C_4)$ alkynyl;
$(C_1-C_4)$ alkoxy;
$(C_1-C_4)$ alkylthio; and
X is O,
p is zero or an integer from one to three; and
$R^5$ is $(C_1-C_3)$ alkyl;
$R^6$ and $R^7$ are independently hydrogen;
$(C_1-C_3)$ alkyl;
$(C_2-C_4)$ alkenyl;
$(C_2-C_4)$ alkynyl; or
phenyl optionally substituted with up to two substituents selected from the group consisting of halogen, nitro, trihalomethyl, $(C_1-C_4)$ alkoxy, and $(C_1-C_4)$ alkyl; or
$R^6$ and $R^7$ can be taken together to form a $(C_5-C_8)$ cycloalkyl group;
$R^8$ is hydrogen or $(C_1-C_3)$ alkyl;
Q is the group

wherein Y is O, S or NH and Z is O or S;
W is phenyl optionally substituted with up to four halogen substituents or optionally substituted with up to two substituents independently selected from the group consisting of halogen, nitro, trihalomethyl, $(C_1-C_4)$ alkyl, $(C_1-C_4)$ alkoxy, $(C_1-C_4)$ alkylthio, $(C_1-C_4)$ alkylsulfinyl, $(C_1-C_4)$ alkylsulfonyl, di$(C_1-C_2)$ alkylamino, $(C_1-C_4)$ alkylcarbonyl and phenylcarbonyl;
n is zero or an integer from one to five;
m is zero or the integer one; and the stabile agronomically acceptable acid addition salts, alkyl halide salts, alkali metal and alkaline earth salts, metal salt complexes, enantiomorphs and racemic mixtures thereof.

2. A compound according to claim 1 wherein A is a group of the formula

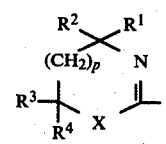

wherein $R^1$, $R^2$, $R^3$ and $R^4$ are independently hydrogen;
$(C_1-C_3)$ unsubstituted alkyl;
$(C_2-C_4)$ alkenyl;
$(C_2-C_4)$ alkynyl;
$(C_1-C_2)$ alkoxy;
$(C_1-C_2)$ alkylthio;
X is O,
p is zero or the integer one or two;
$R^6$ and $R^7$ are independently hydrogen;
$(C_1-C_3)$ alkyl;
$(C_2-C_4)$ alkenyl;
$(C_2-C_4)$ alkynyl; or
unsubstituted phenyl;
$R^8$ is hydrogen or $(C_1-C_3)$ alkyl;
Q is the group

wherein Y is O, S or NH and Z is O or S;
W is phenyl optionally substituted with up to two substituents independently selected from the group consisting of halogen, nitro, trihalomethyl, $(C_1-C_4)$ alkyl, $(C_1-C_4)$ alkoxy, $(C_1-C_4)$ alkylthio, $(C_1-C_4)$ alkylsulfinyl, $(C_1-C_4)$ alkylsulfonyl, di$(C_1-C_2)$ alkylamino, $(C_1-C_4)$ alkylcarbonyl and phenyl carbonyl;
n is zero or an integer from one to three; and
m is zero or the integer one.

3. A compound according to claim 2 wherein A is a group of the formula

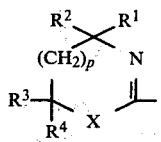

wherein $R^1$, $R^2$, $R^3$ and $R^4$ are independently
hydrogen;
$(C_1-C_3)$ unsubstituted alkyl;
allyl;
propargyl;
methoxy;
methylthio;
X is O,
p is zero or the integer one;
$R^6$ and $R^7$ are independently
hydrogen;
$(C_1-C_3)$ alkyl;
vinyl or allyl;
propargyl; or
unsubstituted phenyl;
$R^8$ is hydrogen or methyl;
Q is the group

wherein Y is O, S or NH and Z is O or S;
W is phenyl substituted with up to two substituents selected from the group consisting of halogen, nitro, trifluoromethyl, methyl, methoxy, methylthio, acetyl and benzoyl;
n is zero or the integer one; and
m is the integer one.

4. A compound according to claim 3 wherein $R^1$, $R^2$, $R^3$ and $R^4$ are independently hydrogen, methyl or ethyl; X is O; $R^6$ and $R^7$ are independently hydrogen, $(C_1-C_4)$ alkyl, allyl, propargyl, or unsubstituted phenyl; $R^8$ is hydrogen; Q is the group

wherein Y is O, S or NH and Z is O; W is phenyl substituted with up to two substituents selected from the group consisting of halogen, methyl, methoxy and trifluoromethyl; and n is zero.

5. A compound according to claim 4 wherein $R^1$ and $R^2$ are methyl; $R^3$ and $R^4$ are hydrogen; p is zero; $R^6$ is hydrogen; $R^7$ is $(C_1-C_4)$ alkyl; and W is phenyl substituted with up to two halogen atoms.

6. A fungicidal composition for controlling phytopathogenic fungi which comprises an agronomically carrier, and as the active ingredient, a fungicidally effective amount of a compound according to claim 1.

7. A fungicidal composition according to claim 6 wherein the phytopathogenic fungi are sclerotial forming fungi.

8. A fungicidal composition according to claim 7 wherein the phytopathogenic fungus is *Botrytis cinerea*.

9. A method for controlling phytopathogenic fungi which comprises applying to a plant, to plant seeds or to the plant habitat a fungicidally effective amount of a compound of claim 1.

10. A method according to claim 9 wherein the phytopathogenic fungi are sclerotial forming fungi.

11. A method according to claim 10 wherein the phytopathogenic fungus is *Botrytis cinerea*.

12. A compound according to claim 1 having the formula

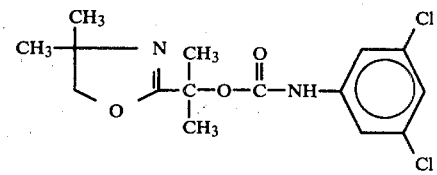

and the stabile agronomically acceptable acid addition salts, alkylhalide salts, alkali metal and alkaline earth salts, metal salt complexes, enantiomorphs and racemic mixtures thereof.

13. A compound of the formula

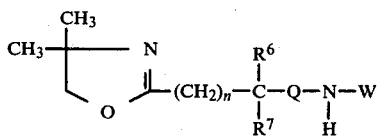

wherein n, $R^6$, $R^7$ and Q are as defined in claim 1 and W is a phenyl optionally substituted with up to four halogen substituents or optionally substituted with up to two substituents independently selected from the group consisting of halogen, nitro, trihalomethyl, $(C_1-C_3)$ alkyl, $(C_1-C_4)$ alkoxy, $(C_1-C_4)$ alkylthio and di$(C_1-C_2)$ alkylamino.

14. A compound of the formula

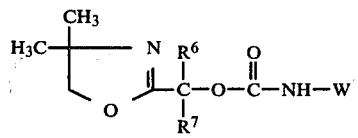

wherein $R^6$ and $R^7$ are independently hydrogen, ($C_1$ to $C_8$) alkyl, phenyl, allyl, or propargyl; and W is a phenyl or naphthyl group or a phenyl group substituted with up to three halogen substituents or optionally substituted with up to two substituents selected from the group consisting of halogen, trifluoromethyl, nitro, phenoxy, or methyl and the agronomically acceptable acid addition salts, alkyl halide salts, alkali metal and alkaline earth salts, metal salt complexes, and enantiomorphs or racemic mixtures thereof.

15. A compound according to claim 14 wherein $R^6$ and $R^7$ are methyl and W is 3,5-dichlorophenyl.

16. A compound according to claim 14 wherein $R^6$ is methyl, $R^7$ is hydrogen and W is 3,5-dichlorophenyl.

17. A compound according to claim 14 wherein $R^6$ and $R^7$ are hydrogen and W is 3,5-dichlorophenyl.

18. A compound according to claim 14 wherein $R^6$ is n-octyl, $R^7$ is hydrogen and W is 3,5-dichlorophenyl.

19. A compound according to claim 14 wherein $R^6$ is phenyl, $R^7$ is hydrogen and W is 3,5-dichlorophenyl.

20. A compound according to claim 14 wherein $R^6$ is phenyl, $R^7$ is allyl and W is 3,5-dichlorophenyl.

21. A compound according to claim 14 wherein $R^6$ is phenyl, $R^7$ is propargyl and W is 3,5-dichlorophenyl.

22. A compound according to claim 14 wherein $R^6$ is methyl, $R^7$ is hydrogen and W is 3,4-dichlorophenyl.

23. A compound according to claim 14 wherein $R^6$ is methyl, $R^7$ is hydrogen and W is 3-chlorophenyl.

24. A compound according to claim 14 wherein $R^6$ is methyl, $R^7$ is hydrogen and W is 2-chloro-5-trifluoromethylphenyl.

25. A compound according to claim 14 wherein $R^6$ is ethyl, $R^7$ is hydrogen and W is 3,5-dichlorophenyl.

26. A compound according to claim 14 wherein $R^6$ is methyl, $R^7$ is ethyl, and W is 3,4-dichlorophenyl.

27. A compound according to claim 14 wherein $R^6$ is n-propyl, $R^7$ is hydrogen and W is 3,5-dichlorophenyl.

28. A compound according to claim 14 wherein $R^6$ is n-butyl, $R^7$ is hydrogen and W is 3,5-dichlorophenyl.

29. A compound according to claim 14 wherein $R^6$ is methyl, $R^7$ is hydrogen and W is 3-methylphenyl.

30. A compound according to claim 14 wherein $R^6$ is methyl, $R^7$ is hydrogen and W is 3,5-ditrifluoromethylphenyl.

31. A compound according to claim 14 wherein $R^6$ is methyl, $R^7$ is hydrogen and W is 3-nitrophenyl.

32. A compound according to claim 14 wherein $R^6$ is methyl, $R^7$ is hydrogen and W is 3-trifluoromethylphenyl.

33. A compound according to claim 14 wherein $R^6$ is methyl, $R^7$ is hydrogen and W is 3-bromophenyl.

34. A compound according to claim 14 wherein $R^6$ is methyl, $R^7$ is hydrogen and W is 3-fluorophenyl.

35. A compound according to claim 14 wherein $R^6$ is methyl, $R^7$ is hydrogen and W is 2,6-dichlorophenyl.

36. A compound according to claim 14 wherein $R^6$ is methyl, $R^7$ is hydrogen and W is 3-phenoxyphenyl.

37. A compound according to claim 14 wherein $R^6$ is methyl, $R^7$ is hydrogen and W is 2,3-dichlorophenyl.

38. A compound according to claim 14 wherein $R^6$ is methyl, $R^7$ if hydrogen and W is phenyl.

39. A compound according to claim 14 wherein $R^6$ is methyl, $R^7$ is hydrogen and W is naphthyl.

40. A compound according to claim 14 wherein $R^6$ is methyl, $R^7$ is hydrogen and W is 2-methyl-3-chlorophenyl.

41. A compound according to claim 14 wherein $R^6$ is methyl, $R^7$ is hydrogen and W is 2,5-dichlorophenyl.

42. A compound according to claim 14 wherein $R^6$ is methyl, $R^7$ is hydrogen and W is 2,4,5-trichlorophenyl.

43. A compound according to claim 14 wherein $R^6$ is methyl, $R^7$ is vinyl, and W is 3,5-dichlorophenyl.

44. A compound according to claim 14 wherein $R^6$ is methyl, $R^7$ is hydrogen and W is 3,4,5-trichlorophenyl.

* * * * *

UNITED STATES PATENT AND TRADEMARK OFFICE
CERTIFICATE OF CORRECTION

PATENT NO. : 4,378,357

DATED : March 29, 1983

INVENTOR(S) : George A. Miller et al.

It is certified that error appears in the above-identified patent and that said Letters Patent is hereby corrected as shown below:

Col. 4, line 28, "interger" should read -- integer --.
Col. 8, line 53, "catayst" should read -- catalyst --.
Col. 8, line 68, "ar" should read -- are --.
Col. 9, line 45, "utiilized" should read "-- utilized --.
Col. 12, line 17, "nitrophenyl))" should read -- nitrophenyl) --.
Col. 12, line 68, "pass" should read -- past --.
Col. 15, line 2, "Example B 2B," should read -- Example 2B --.
Col. 33, lines 35-40, CLAIM 1,

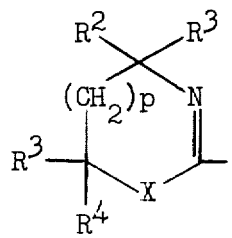   should read   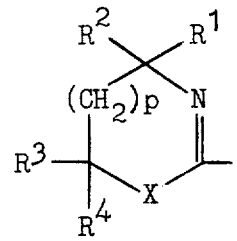

Signed and Sealed this

Seventeenth Day of January 1984

[SEAL]

*Attest:*

*Attesting Officer*

GERALD J. MOSSINGHOFF

*Commissioner of Patents and Trademarks*